United States Patent [19]
Collin

[11] Patent Number: 5,770,205
[45] Date of Patent: Jun. 23, 1998

[54] TISSUE FRACTIONS OF SEA CUCUMBER FOR THE TREATMENT OF INFLAMMATION

[75] Inventor: Peter Donald Collin, Sunset, Me.

[73] Assignee: Coastside Bio Resources, Stonington, Me.

[21] Appl. No.: 692,174

[22] Filed: Aug. 5, 1996

[51] Int. Cl.$^6$ .............................. A01N 65/00; C07G 3/00
[52] U.S. Cl. .......................................... 424/195.1; 536/4.1
[58] Field of Search ........................... 424/195.1; 536/4.1

[56] References Cited

FOREIGN PATENT DOCUMENTS 295037  8/1993  European Pat. Off. .

OTHER PUBLICATIONS

Yaacob et al. Malaysian Applied Biology 24(1) pp. 23–28, 1995.

Eylers, John P., Ion–Dependent Viscosity of Holothurian Body Wall and Its Implications for the Functional Morphology of Echinoderms. *J. Exp. Biol.*, 99:1–8 (1982).

Findlay, John A., Frondogenin, A New Aglycone From the Sea Cucumber *Cucumaria Frondosa*. *J. Natural Prod.*, 47(2):320–324, Mar.–Apr.(1984).

Robert, Andre et al., The Granuloma Pouch as a Routine Assay for Antiphlogistic Compounds. *Acta Endocrinologica*, 25:105–112 (1957).

*Primary Examiner*—Leon B. Lankford, Jr.
*Attorney, Agent, or Firm*—Rothwell, Figg, Ernst & Kurz

[57] ABSTRACT

The present invention relates to fractions of sea cucumbers (*Phylum Echinodermata*, Class Holothuroidea), particularly those derived from the epithelial layers and the flower portion, that markedly inhibit inflammation in laboratory animals and show significant subjective benefit in humans with inflammation disorders such as arthritis, and methods for preparing the same.

32 Claims, 3 Drawing Sheets

TISSUE FRACTIONS OF SEA CUCUMBER FOR THE TREATMENT OF INFLAMMATION

FIELD OF THE INVENTION

The present invention relates to compositions for treating warm-blooded animals afflicted with inflammation disorders. More particularly, the present invention relates to the treatment of certain inflammatory conditions in patients, by administering distinct fractions of the echinoderm sea cucumber which consists of:

1. the isolated body wall of the sea cucumber, or its active derivatives;
2. the epithelial layer of the sea cucumber body wall, or its active derivatives,
3. the anterior flower or mouth portion of the sea cucumber, or its active derivatives, or
4. combinations thereof.

BACKGROUND OF THE INVENTION

Mammals are known to suffer from various conditions involving inflammation with concomitant swelling, tenderness, decreased mobility, pain and fever. While a number of anti-inflammatory agents are effective in the symptomatic treatment of such inflammatory conditions as Rheumatoid Arthritis, Rheumatoid Spondylitis, Osteoarthritis, degenerative joint diseases, and the like, many such agents have a number of undesirable side effects, such as gastric irritation and the like.

The etiology and pathogenesis of rheumatic and arthritic diseases remain obscure. Meanwhile, the need continues for safer, better calibrated drugs which will slow the process and alleviate the symptoms of inflammatory diseases. For example, in Rheumatoid Arthritis, any agent which reduces inflammation is important in lessening or delaying the development of crippling.

It is the object of this invention to provide a new method for treating inflammatory conditions and slowing the development of arthritic conditions, without the side effects associated with previous treatments.

SUMMARY OF THE INVENTION

This invention provides a method of treating inflammation disorders in a warm-blooded animal in need of such treatment which comprises administering to said warm-blooded animal a therapeutically effective amount of a composition comprising the isolated body wall of a sea cucumber, the isolated epithelial layer of the body-wall of the sea cucumber, the flower of the sea cucumber, their active derivatives or mixtures thereof.

It has been found that these portions of the sea cucumber dramatically inhibit inflammation in laboratory animals in assays which are known in the medical field as being acceptable in providing relevant data and valid indications of therapeutic efficacy for subsequent development and medical use of active compositions.

DETAILED DESCRIPTION OF THE INVENTION

Figure 1A:
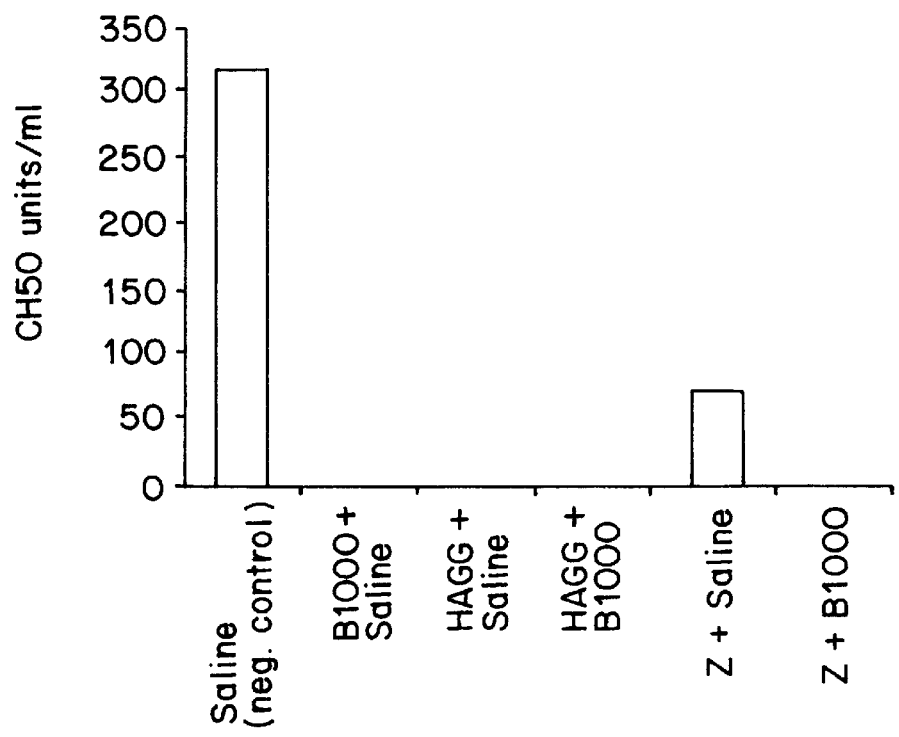
FIGS. 1 A–D—Graphs showing inhibition of classic complement pathway by B1000 according to four different parameters.

The sea cucumbers constitute the taxonomic Class Holothuroidea, Phylum Echinodermata. They possess an elongated body comprising a thick, leathery body wall of epithelial and collagenous layers surrounding the internal organs or viscera, an anterior mouth surrounded by numerous retractile tentacles (herein referred to as the "flower"), and a posterior portion comprising cloaca and anus. Muscle bands are found along the length of the interior surface of the body wall.

Sea cucumbers are a well-known Chinese delicacy harvested from many areas of the world and are a valuable trading resource in Chinese-speaking countries. There are a number of patent applications by Chinese groups relating to sea cucumbers as nutritional supplements (e.g., Chinese application CN 1065019) and patents or applications from Japanese groups relating to various carbohydrate moieties from sea cucumber as anticoagulants (JP 94070085 B2; WO 9008784) and as active components for treating AIDS (WO 9202231; WO 9009181). Historically, sea cucumbers for the worldwide market have been harvested, boiled with the muscles intact, and then salted and dried over an open flame. Salting and drying are the traditional methods of obtaining a product that is safe for storage and transportation. Nutritional supplements have been prepared by finely dividing these salted and fire-dried sea cucumber body walls for use in encapsulated products.

Pharmaceutical companies are expanding efforts to screen and assay biologically active compounds from natural sources. The term that has been applied to this discovery process is "bio-prospecting." When bio-prospecting is successful in finding and identifying promising compounds, efforts are then made to determine and perfect the process by which the compound is produced in its active form. Useful processes develop from these bio-prospecting discoveries, as well as useful compositions of matter and methods of using the same.

Sea cucumber tissue has been found to contain numerous compounds having potential as biologically active agents in medical and veterinary applications. These include sulfated polysaccharides (e.g. fucosylated chondroitin sulfate, Viera & Mourao, JBC, vol. 263, pp. 18176–83 (1988)) sterol glycosides, saponins (e.g., frondogenin and its glycosides, Findlay et al., J. Natural Products, vol. 47, pp. 320–324 (1984)), lactones (e.g., triterpenoid lactones, their acetates and glycosides, Findlay et al., supra), peptides, protamines, glycogens, saccharides (e.g. fucose, galactosamine, glucuronic acid, quinovose, xylose or o-methylglucose, Findlay et al., supra), polysaccharides (e.g., polyfucose sulfate, WO 9202231) and various amorphous compounds rich in saccharide moieties (Findlay et al., supra). Fractions derived from sea cucumber have now been found to possess strong anti-inflammatory activity. This anti-inflammatory property can be used in numerous applications in research and medicine, particularly those relating to rheumatic and arthritic conditions, serine protease-mediated inflammation and the classic complement cascade.

As used herein, the term "sea cucumber" refers to any species of the Phylum Echinodermata, Class Holothuroidea, such as species of the genera Actinopyvga (e.g., A. lacanora, L. echinites), Cucumaria (e.g., C. frondosa, C. echinata, C. chronhjelmi), Eupentacta (e.g., E. quinquesemita), Halodeima (e.g., H. cinerascens), Holothuria (e.g., H. pervicax, H. atra, H. edulis, H. scabra, H. monoacaria, H. leucospilota), Leptosynapta (e.g., L. inhaerens), Ludwigothuria (e.g., L. grisea), Microthele (e.g., M. nobilis), Molpadia (e.g., M. musculus), Parastichopus (e.g., P. nigripunctatus), Paracaudina (e.g., P. chilensis), Pelagothuria, Pentacta (e.g., P. australis), Polycheira (e.g., P. rufescens), Psolus (e.g., P. chitonoides), Stichopus (e.g., S.

*japonicus, S. chloronovus, S. variegatus*), Synapta (e.g., *S. maculata*), Thelenota (e.g., *T. ananas*) or Thyone (e.g., *T. briareus*);

the term "flower" refers to the anterior portion of the sea cucumber comprising the mouth and retractile tentacles;

the term "B1000" refers to the isolated epithelial layer of the sea cucumber, substantially free of the flower portion, muscle, collagenous tissues and viscera;

the term "T2000" refers to the isolated flower portion of the sea cucumber, substantially free of other portions of the sea cucumber body;

the term "active derivative" refers to any compound, fraction or combination thereof, derived from a sea cucumber fraction described herein that has anti-inflammatory activity;

the term "inflammation disorder" refers to any condition or disease in a warm-blooded animal having inflammation as a symptom or proximate cause.

Active anti-inflammatory compositions can be obtained from sea cucumber in a variety of ways. For example, sea cucumbers can first be cleaned of muscle bands and viscera, boiled (but not salted), preferably for about ½ hour, and then dried, preferably in low-heat mechanical driers such as those employing "heat pump" technology. The dried tissue can further be ground or divided as needed for ultimate use. This process decreases the sodium content of the tissue and helps protect various active ingredients from degradation. This fraction can be formulated and used directly as an anti-inflammatory composition, either above or in combination with other sea cucumber fractions, or as a raw material for further purification of active derivatives. A commercial sea cucumber body wall preparation is available from Coastside Bio Resources under the tradename "Ginseng of the Sea™."

Another active fraction can be obtained from the flower portion of the sea cucumber. During the evisceration process described above, the anterior portion ("flower") of the sea cucumber is cut away from the viscera and body wall. The isolated flower is then heated, preferably for about ½ hour, dried at low temperatures (e.g. between about 140° F. and about 180° F. using conventional drying apparatus and per se known techniques). This dried fraction, designated "T2000" by the inventor, can then be ground or divided as needed for formulation and use directly as an anti-inflammatory composition, either alone or in combination with other sea cucumber fractions, or as a raw material for purification of active derivatives. The method and extent of division of the material is not critical to the invention, and can readily be determined by those skilled in the art according to the manner in which the composition will be used.

Still another anti-inflammatory fraction can be obtained from the epithelial layer of the sea cucumber body wall. Muscle, viscera and flower are removed as described above, followed by isolation of the epithelial layer of the sea cucumber body wall from the harder collagenous layers beneath, preferably by one or more of the following means:

heating the body-wall in water at temperatures from about 140° F. to about 180° F., preferably at about 170° F., followed by mechanical separation by hand or machine (e.g., using machines known in the art as mincers or de-boners, which detect tissue density and separate harder tissues from softer tissues);

enzymatic hydrolytic separation, using, e.g., organism's own digestive tract enzymes, proteases from mammalian sources, proteases from nonmammalian sources or acidic hydrolazes, preferably Alcalase (NOVO Nordisk Bio Chem, North Carolina), the enzyme preferably being in a solution of about 1% to about 10% enzyme, most preferably in a solution of about 10% enzyme;

scouring/scrubbing or de-boning processes known to those skilled in the potato or chicken processing arts. Heating in water, followed by mechanical separation using a de-boner is most preferred.

The epithelial fraction so obtained (designated "B1000" by the inventor) is a dark, moist, viscous, carbohydrate-rich matter. B1000 can be dried as described above, formulated and used directly as an anti-inflammatory composition, either alone or in combination with other sea cucumber fractions, or used as a raw material for the purification of active derivatives.

One embodiment of the present invention is the use of fractions derived from sea cucumber as inhibitors of detrimental aspects of mast cell products at a site of inflammation, based on their activity as serine protease inhibitors. Mast cells have been found to be implicated in diseases and events such as allergic and non-allergic Rhinitis, Atopic Dermatitis, including Psoriasis, Crohn's Disease, Cluster headaches, and Coronary Artery Spasm. It is now recognized that mast cells are implicated in the pathophysiology of inflammatory skin diseases as well as in other physiological disorders. Neutrophils as indirect mast cell products in an inflammatory response are a main source of serine proteases which are important in the tissue damage resulting from inflammation. Sea cucumber fractions, found to act as inhibitors of neutrophil rich granuloma in an antiphlogistic compound bio-assay such as that disclosed in Roberet, et al., *Acta Endocrinologica*, vol. 25, pp. 105–112 (1957) (incorporated herein by reference), can be considered to have specific activity for mast cell mediators or the proteases derived therefrom.

Serine protease inhibitors have been found to play a major role in the direct inactivation of the mediators of inflammation so that the normal wound healing process can be accelerated without interference from the excess of materials released at the site of inflammation. The activity of sea cucumber fractions as inhibitors of serine protease would also make them useful deactivators of those mediators of inflammation which may not yet be recognized or are found in association with a particular disease.

Another embodiment of the present invention is the use of sea cucumber fractions to inhibit the blood protein C1 of the Classical Complement portion of the immune system. This activity of Classical Complement inhibition is a component of a direct or indirect biological pathway of inflammation inasmuch as various portions of the Classical Complement cascade are being inhibited which would otherwise trigger inflammatory responses.

Still another embodiment of the present invention is the use of sea cucumber fractions in humans to produce a subjective benefit in cases of decreased range of motion or arthritis inflammation.

The sea cucumber fractions of the present invention may be in the form of powders, capsules, liquids, suspensions, ointments, or any other means of delivery which those skilled in the arts would deem appropriate. The formulation is dictated by the application, e.g., an application wherein a skin malignancy is treated might call for a topical formulation, whereas treatment of a liver malignancy might call for a formulation suitable for direct injection into the site of malignancy. It is well with the skill of the medical and veterinary arts to determine a suitable formulation for any particular application. For example, a topical ointment would be most appropriate for treatment of arthritic inflammation of the hands, while a rectal formulation might be most effective for treated inflammation of the colon. Furthermore, methods of making such formulations are well-known in the art (see, e.g. *Remington's Pharmaceutical Sciences,* 18th ed., Mack Publishing Co., Easton, Pa. (1990)). The anti-inflammatory compositions of the present invention may be administered orally, topically, rectally or via injection, alone or in mixture with an excipient or a carrier as set forth above and in accordance with the particular purpose of use. The active ingredient can be within a range of from about 0.01 to about 100 w/w %, preferably from about 2 to about 80 w/w %. The dose per day thereof, also depending upon the particular use to which the composition is put, the frequency of administrations, the form of medicament, the symptoms, age and body weight of the recipient of the composition, can be within the range of about 0.1 to about 1,500 mg of the effective ingredient per kg of body weight, preferably from about 1 to about 1,000 mg/kg, and most preferably about 10 mg of the effective ingredient per kg of body weight. The daily dosage of administration may be divided into two to four separate doses.

The following examples are intended to illustrate, but in no way to limit, the invention set forth in the claims.

EXAMPLE 1

Preparation of Whole Body Wall From Sea Cucumber

Muscle meat, viscera, anterior and posterior portions of the sea cucumber *Cucumaria frondosa* were removed in order to leave a sea cucumber body wall free of most, if not all of the above named portions. The thus obtained body wall was boiled for about ½ hour in fresh water and dried in a low heat utilizing a 40 hp "heat-pump" dryer (Southwind Mfg., Nova Scotia, Canada). The body wall fraction was dried to about 3% moisture and finely divided.

EXAMPLE 2

Mechanical Extraction and Processing of Sea Cucumber Epithelium

A fraction termed B1000, consisting of sea cucumber epithelium, was produced by the following method. The anterior, posterior, viscera and muscles were removed from sea cucumbers of the species *Cucumaria frondosa* to obtain an isolated body wall. Body wall portions thus obtained were heated for about 30 minutes in fresh 170° F. water, then cooled on wire racks to room temperature. Next, the body wall portions were passed through an industrial machine known to those in the food processing arts as a deboner or mincer (Paoli Machine, Illinois). The deboner was adjusted to separate the softer outer epithelial layer from the harder collagenous portion of the body wall. The black viscous layer of the epithelium so separated, designated B1000 by the inventor, was dried by conventional means using a 40 hp "heat pump" dryer as in Example 1 to approximately 3% moisture content and finely divided to obtain a powder.

EXAMPLE 3

Enzymatic Extraction and Processing of Sea Cucumber Epithelium

Enzymes were used to help separate the epithelial layer from the harder collagenous inner layer of body walls from sea cucumbers of the species *Cucumaria frondosa*. The body wall portions were isolated and heated in water as described in Examples 1 and 2. They were then soaked in a solution of 10% Alcalase enzyme (NOVO Nordisk Bio Chem, North Carolina) in fresh water at a temperature of 130° F. (±30° F.). The time of soaking depended on the condition of the particular lot of body walls and their characteristics, and varied from about 15 min. to about 3 hours. The average time soaking in the enzyme solution was about one half hour. The body walls were then removed from the enzyme solution and processed by hand to further isolate the black epithelial layer B1000 from the underlying collagenous tissues. The B1000 thus obtained was dried and powdered as in Examples 1 & 2.

EXAMPLE 4

Extraction and Processing of Sea Cucumber Flower

A fraction termed T2000, derived from the sea cucumber flower, was obtained in the following manner.

During the processing operation of removing viscera and muscle set forth in Examples 1 and 2, the anterior portion of the sea cucumber *Cucumaria frondosa* was removed, taking care to include the mouth portion of the head with surrounding tentacles, which is a tissue rich in calcium carbonate (among other compounds). This separated flower portion was then boiled for about ½ hour to obtain the fraction designated T2000 by the inventor. The T2000 was then dried in a conventional heat-pump dryer as in Examples 1–3 and finely divided.

EXAMPLE 5

Preparation of Derivative Fractions of B1000 and T2000

The finely divided powders of epithelial layer (B1000) and flower fraction (T2000) obtained in Examples 2 and 4, respectively, were further processed by mixing in an aqueous solution and rotating for 12 hours with a magnetic stirrer. The resultant solution was centrifuged at 30,000 RPM for one hour and the supernatant was removed and lyophilized.

EXAMPLE 6

Antiphlogistic Activity of B1000 and T2000 as Determined by the "Rat Granuloma Pouch Assay"

Method: Roberet, A. and J. E. Nezamis, "The Granuloma Pouch as a Routine Assay for Antiphlogistic Compounds," Acta Endocrinologica: 25, p. 105–112 (1957) (incorporated herein by reference).

Procedure: Thirty-nine Sprague-Dawley male white rats, weighing about 300–350 grams each, were used in the test. They were divided into 7 groups of 5 rats each and 1 group of 4 rats.

The rats were confined to individual cages in the animal room. The temperature was maintained at 23° C.±1° C. The rats had free access to Rodent Teklad Laboratory Diet and fresh water at all times. The rats did not have any disease or exhibit any abnormalities.

The rats were clipped over their dorsal surface with a pair of fine electric clippers. The rats were then anesthetized with Sodium Pentobarbital, given intraperitoneally (0.5 ml equivalent to 3 mg). Using a sterile syringe, 25 ml of air was injected under the skin to produce a pneumoderma. All the pouches were made just over the shoulder blades. This was followed by 0.5 ml of a sterile 1% solution of croton oil made up in corn oil, injected directly into the pouch.

Samples were prepared by mixing powdered B1000, T2000, or sea cucumber body wall fraction with corn oil. All of the rats were treated for a total of five days with the respective compounds made up on a volume of 0.25 ml. All treatments were given by gavage. Dose was 10 mg/kg body weight.

After five days of treatment, the rats were sacrificed and the volume of exudate was measured with a hypodermic syringe. Scissors were used to open each pouch to be certain that all of the exudate had been removed. The results are summarized in Table I.

TABLE I

Comparison of treatment groups, average pouch exudates and body weight gains. Dose - 10 mg/kg body weight.

| Group | Treatment | No. Rats Per Group | Pouch Exudate (ml) | Mean Body Weight (g) |
|---|---|---|---|---|
| I | Neg. control - water | 5 | 9.48 | +21.2 |
| II | Pos. control - hydrocortisone | 5 | 3.74 | −32.4 |
| III | T2000 | 5 | 2.88 | +12.0 |
| IV | B1000 | 5 | 2.86 | +5.4 |
| V | sea cucumber body wall | 5 | 6.84 | −7.0 |
| VI | sea cucumber body wall | 5 | 4.18 | −15.0 |
| VII | sea cucumber body wall | 5 | 6.14 | +4.0 |
| VIII | sea cucumber body wall | 4 | 6.70 | +1.0 |

Pouch Exudate: The average pouch exudate varied from 9.48 ml in the water treated group (negative control) to 2.86 ml in the B1000 treated group. T2000 gave an exudate value of 2.88 ml. These were excellent values compared to the positive control, hydrocortisone 3.74 ml). In fact, they were better than 10 mg/kg of hydrocortisone but without the weight loss seen in the hydrocortisone treated group.

The other sea cucumber preparations had average pouch exudate values 4.18–6.84 ml per rat. These were better values than the negative control of 9.48 ml. It is difficult to correlate the weight loss or low weight gain with the anti-inflammatory activity.

Body Weights: Body weight gain ranged from 21.2 for the negative control to a weight loss of 32.4 g. per rat in the hydrocortisone treated group.

The T2000 group and the B1000 group had weight gains of 12 grams and 5.4 grams, respectively. Both these groups showed excellent anti-inflammatory response. Groups treated with sea cucumber body wall had both weight gains and weight losses.

It appears that the anti-inflammatory effect is unrelated to the weight loss in the sea cucumber products in the treated groups, sea cucumber products. There must be other growth inhibition present.

Summary: The rat granuloma pouch test for anti-inflammatory activity of various sea cucumber fractions or extracts, when compared to a negative control (water) and a positive control (hydrocortisone) indicate the following:

1. T2000 and B1000 have an anti-inflammatory activity better than 10 mg. hydrocortisone.

2. The mean exudate for the water control was 9.48 ml and for the hydrocortisone treated group was 3.74 ml.

3. Sea cucumber body wall caused pouch exudate up to 4.18 ml, which indicates it is almost as good as 10 mg hydrocortisone per kilogram body weight.

EXAMPLE 7

Anti-inflammation Activity of B1000 as Determined in a Mouse Model of *P. aeruginosa* Infection Inflammation Materials and Methods Bacterial strains and preparation of inocula: *P. aeruginosa* 6294 was kept frozen at −85° C. as individual aliquots in trypticase soy broth with 15% glycerol. The bacteria from these frozen stocks were inoculated onto trypticase soy agar overlaid with a 12,000 MW cutoff dialysis membrane {836}. After overnight growth, the bacteria were harvested from the membranes with a sterile cotton swab and suspended in sterile 1% proteose peptone to an optical density at 650 nm of 0.92 to achieve a bacterial concentration of approximately $2 \times 10^9$ cfu/ml. The bacteria were diluted 1:10 sterile 1% proteose peptone to achieve the desired final concentration. The actual bacterial concentration was confirmed by plating of appropriate dilutions, in duplicate, onto Maconkey's agar. The dose of 6294 required to establish infection in 50% of mice challenged with this strain (ID50 value) is $1.93 \times 10^5$ cfu (95% confidence interval; $3.25 \times 10^4$–$16.6 \times 10^5$). Thus, the challenge dose for this experiment is approximately 50 times the ID50 value.

Infection of Mice: C3H/HeN female mice (8 weeks old) were obtained from Charles River Breeding Laboratories, Wilmington, Mass. Groups of 5 mice were given an intraperitoneal injection of 0.2 ml of a cocktail containing 6.7 mg of ketamine hydrochloride (Parke Davis, Morris Plains, N.J.) and 1.3 mg of xylazine (Haver, Shawnee, Kan.) per ml. After the animals were anesthetized, they were placed under a stereoscopic microscope, and three 1-mm-long scratches were made in the corneal epithelium and superficial stroma with a 27-gauge needle. Care was taken not to penetrate the stroma to the anterior eye chamber. The bacteria were immediately inoculated onto the abraded cornea in a 5-$\mu$L volume dispensed from a micropipette. The mice usually regained consciousness 15–25 minutes after inoculation. All procedures were in accordance with the Association for Research in Vision and Ophthalmology Resolution on the Use of Animals in Research and were approved by the Harvard Medical Area Standing Committee on Animals.

Grading of corneal infection: Infected eyes were graded every 24 hours after inoculation for a total of six days by an investigator unaware of the treatments that the groups received. The following grading scheme was used: grade 0, eye macroscopically identical to the uninfected contralateral control eye; grade 1, faint opacity partially covering the pupil; grade 2, dense opacity covering the entire anterior segment; grade 4, perforation of the cornea and/or phthisis bulbi (shrinkage of the eyeball following inflammatory disease).

Preparation of derivative fraction of B1000 and administration to mice: Powdered B1000 was dissolved in sterile distilled water at a concentration of 10 g in 100 ml (10%). The sample was mixed by stirring overnight on a magnetic stirrer. The insoluble material was pelletted by centrifugation at 13000×g for 30 min. and the supernatant was harvested and lyophilized. Approximately 1.6 grams of material were recovered after lyophilization.

Treatment of Mice: B1000 derivative was prepared as described above. The lyophilized powder was dissolved in the drinking water at a concentration of 200 µg/ml, sterilized by filtration through a 0.45 µm filter and put in sterilized water bottles. The bottles were given to the mice immediately after infection. The mice were given a fresh preparation of B1000 derivative in new water bottles after 3 days.

Statistical analysis: Mann-Whitney U test for non-parametric data was used to determine the statistical significance of the corneal scores on the given days.

Results: The results of the macroscopic grading of the infected eyes in the treated and untreated groups are shown in Table II.

TABLE II

| Days post infection | corneal scores | corneal scores | Significance |
|---|---|---|---|
| 1 | 1,1,1,1,1 | 2,2,2,2,2 | p = .009 |
| 2 | 1,1,2,2,2 | 2,3,3,3,3 | p = .0216 |
| 3 | 1,1,3,3,3 | 3,3,3,3,3 | not significance |
| 4 | 1,1,3,3,3 | 3,3,3,3,3 | not significance |
| 5 | 1,1,3,3,3 | 3,3,3,3,3 | not significance |
| 6 | 1,1,3,3,3, | 3,3,3,3,3 | not significance |

These data indicate that a derivative of B1000 significantly reduced inflammation as indicated by the reduced corneal scores on the first two days after infection with $10^7$ cfu per eye with *P. aeruginosa* 6294. After 48 hours, although there was a trend toward reduced inflammation these groups were not significantly different.

EXAMPLE 8

Inhibition of Tissue Plasminogen Activator by B1000

B1000 prepared as in Example 5 was assayed for its ability to inhibit tissue plasminogen activator by performing a zymographic analysis of conditioned medium from C8161 human melanoma Cells treated with 1, 10 and 100 µg B1000/ml Twenty-four hour serum-free conditioned media from the upper wells of the Membrane Invasion Culture System containing C8161 human melanoma cells with and without different concentrations of B1000 (lanes –4) were mixed 2 parts to 1 part Laemmli sample buffer minus reductant. Without prior boiling, 35 µl of these samples were loaded onto a 10% polyacrylamide SDS-gel containing 0.1% gelatin plus plasminogen in the resolving gel and no gelatin/plasminogen in the stacking gel. After electrophoreses, the gels were incubated at room temperature in 50 mM Tris-Cl pH 7.5 plus 2.5% Triton X-100 for 30 minutes with gentle shaking, then incubated for 25 hours in 100 mM glycine pH 8.3/10 mM EDTA at 37° C. After staining with Coomassie Brilliant Blue R-250 (0.25%) in 25% isopropanol/10% acetic acid for 30 minutes, the gel was destained in 10% methanol/10% acetic acid until the was remained clear. A diminution in the tissue plasminogen activator (tPA) double was seen at approximately 65 kDa) with increased dosages of B1000.

EXAMPLE 9

Inhibition of Complement by a Derivative of B1000

Preparation of B1000 derivative: B1000 was pulverized with a mortar and pestle and put into a tube containing 0.15M NaCl at a weight to volume ratio of 100 µg/ml. The tube was rotated to mix at room temperature overnight and the following morning it was centrifuged to spin down the undissolved material. The supernatant was removed, and after final filtration through a 0.22 µm filter, the B1000 derivative was put into a sterile tube, capped tightly and stored at 4° C.

The undissolved material was dried and weighted, and about half was found to have gone into solution. Culture of the unfiltered B1000 derivative on blood agar plates yielded several colonies of at least two different bacterial species, which were not further identified.

Experiment with complement inhibition: Blood was collected from a healthy donor and allowed to clot at room temperature for 60 minutes. The serum was removed from the blood clot, and transferred to a clean tube.

Complement activators with known activities were prepared as positive controls. These included heat-aggregated gamma globulin (63° C., 30 minutes) and zymosan. The former (HAGG) is a potent activator of the classical pathway, and also activates the alternative pathway weakly. The latter (Z) consists of boiled and washed bakers' yeast and is a strong activator of the alternative pathway. HAGG was used at 14 mg/ml and Z at 10 mg/ml. These are relatively high doses. The B1000 extract was used straight.

The experiment was done by mixing 8 parts of the normal human serum (NHS) with 2 parts saline, saline plus activator (or B1000 extract), or activator plus B1000 extract. These mixtures were incubated for 30 minutes at 37° C. and the complement was examined by assaying total complement activity (CH50), C4d, Bb and iC3b split products. Results are shown in Table III.

TABLE III

| Incubation mixture | CH50 | C4d | Bb | iC3b |
|---|---|---|---|---|
| NHS + saline (neg control) | 318 | 5.33 | 2.3 | 119.0 |
| NHS + HAGG + saline | 0 | 25.75 | 32.67 | 861.0 |
| NHS + Z + saline | 75 | 6.43 | 57.45 | 585.0 |
| NHS + B1000 + saline | 0 | 4.38 | 17.32 | 115.5 |
| NHS + HAGG + B1000 | 0 | 5.92 | 36.84 | 242.5 |
| NHS + Z + B1000 | 0 | 4.52 | 74.17 | 436.3 |

Figure 1B:
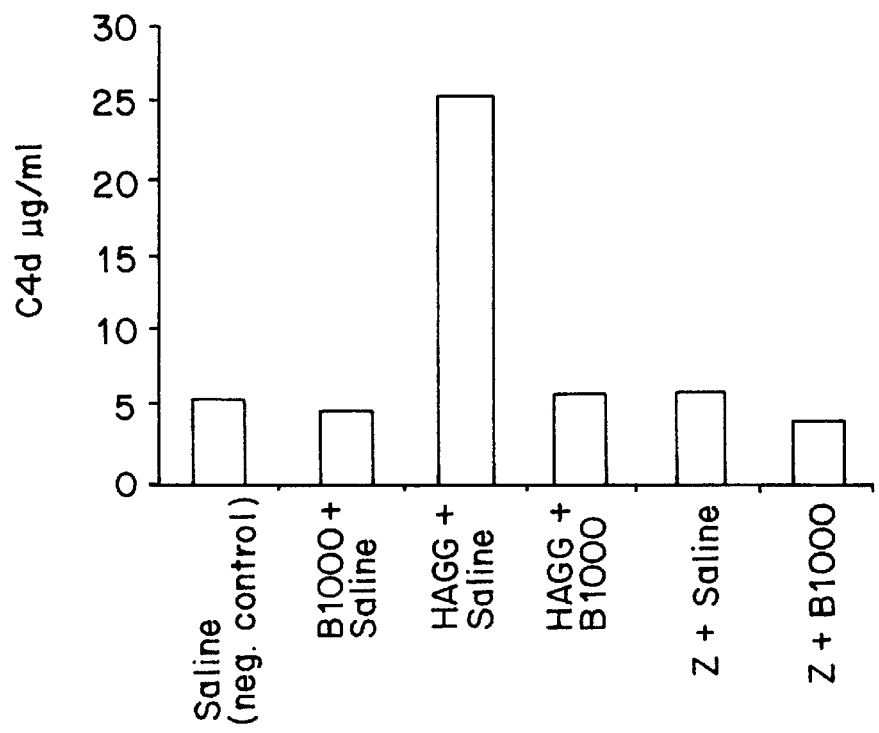
Figure 1C:
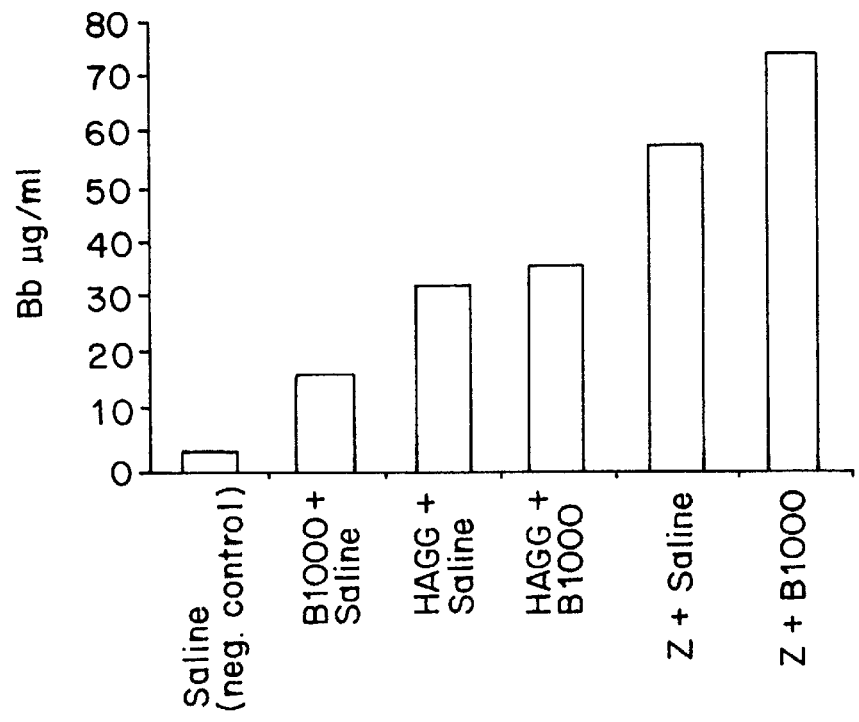
Figure 1D:
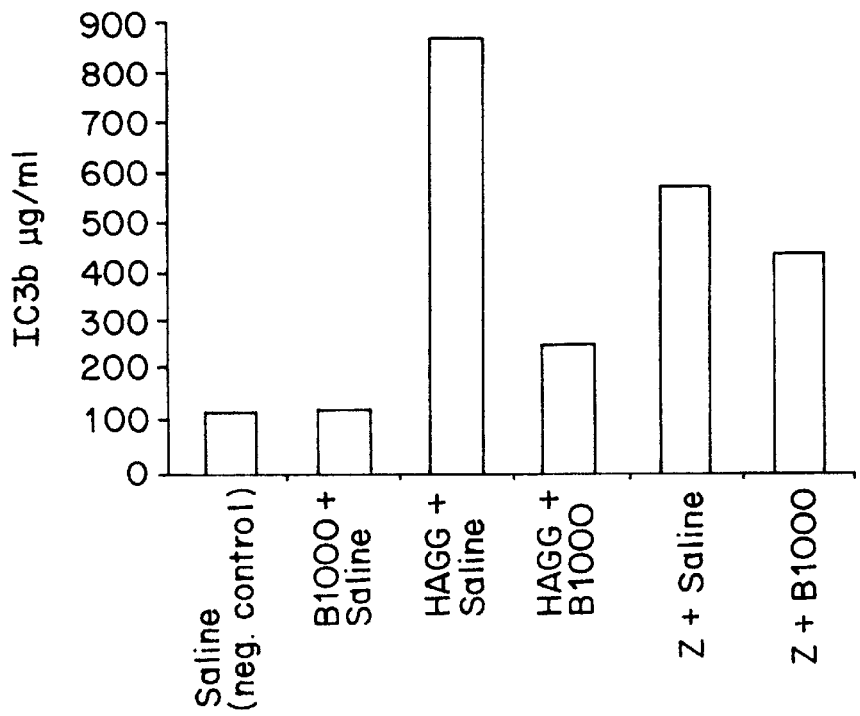

FIGS. 1A–D are graphic representations of the data of Table 3. It can be seen in FIG. 1A that the B1000 by itself inhibited the classical pathway activation necessary for CH50 activity. In FIG. 1B, the C4d assay, the HAGG caused a good increase of C4d which it is supposed to do (classical pathway activation) but this increase in C4d was blocked by the B1000. In the Bb assay, there was some activation of the alternative pathway by B1000. This could be due to the polyanions or it could be due to endotoxins released from the contaminating bacteria (which were filtered out, but any soluble products from them would still have been present). There was no decrease in Bb produced by the HAGG or Z, and the increase seen was probably an additive effect of the B1000 activation by itself. In the iC3b assay, it appeared that the B1000 did nothing by itself and that it blocked most of the HAGG-, and some of the Z-mediated iC3b production.

Figure 2:
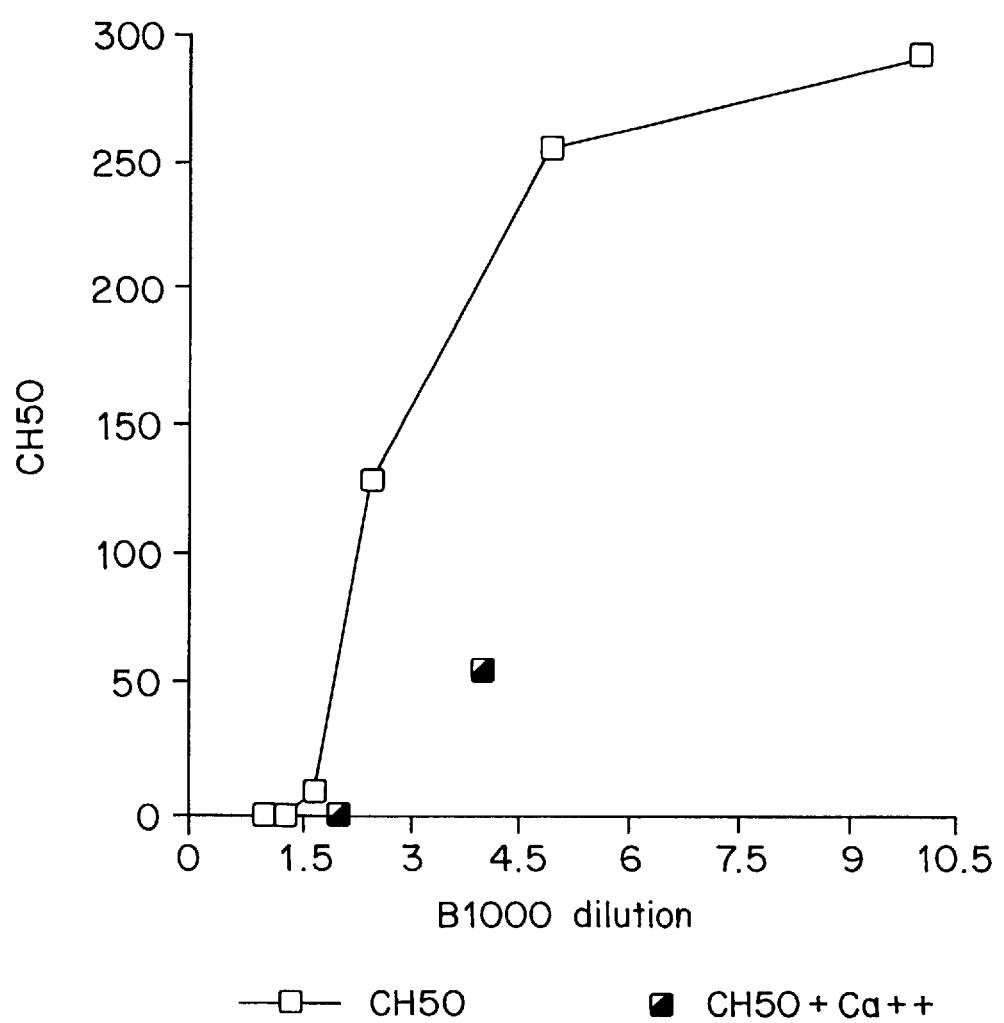
FIG. 2—Effect of B1000 on total complement activity (CH50).

Dose-response of B1000 effect on CH50: In order to find a dose of B1000 that didn't block 100% of the CH50 response (to determine when a slight change is happening in other assays) we mixed NHS (as above) with dilutions of B1000 made in saline. These were incubated at 37° C. for 30 minutes, and then the CH50 assay was done. Results are shown in FIG. 2.

EXAMPLE 10

Nine subjects exhibiting moderately severe to severe arthritic pain were given Ginseng of the Sea™ sea cucumber body wall preparation for periods ranging from 8 to 16 weeks. All patients used a 500 mg capsule supplement orally in the following manner: 3 capsules in the morning and 3 capsules in the evening for 3 weeks, then 2 capsules in the morning and 2 in the evening subsequently. Occasionally, as noted, the patients reduced to 2 capsules per day after the target joint was significantly improved for maintenance supplementation.

A rating scale of 1 to 10, with 1 being very mild and occasional pain which does not limit activity in any way, to 10 which is severe, continuous pain which prevents normal activity, is used as a subjective pain measurement tool in this study.

An 81 year old gentleman presented with left shoulder adhesive capsulitis of one year duration. He rated the pain as a 7 with inability to abduct of forward flex the left shoulder. Dressing was very painful. After 8 weeks supplementation beginning in January, 1996 he rated the pain as a 1 and could fully abduct the shoulder and fully extend the shoulder to a full reach above his head with only minimal pulling feeling. No chiropractic treatments were given to the shoulder.

A 50 year old female presented with cervical spine arthritis of 6 years duration. Radiographs revealed cervical degenerative disc and joint disease at C5, 6 and 7. Pain was rated at 5. She had loss of range of motion. She had been treated for 18 months with temporary resolution of cervical joint pain subsequent to adjustment. Following 12 weeks of supplementation beginning October, 1995 she rated the pain as 2 and had markedly increased ROM of the cervical spine.

A 44 year old male presented with chronic thoracic spine pain of 13 years, status post lifting injury at work. Radiographs revealed degenerative joint disease with loss of disc height and osteophyte formation at T10, 11 and 12. There was hyper-kyphosis at this level. He has been treated once per month for chronic mid-back pain and spasm for 10 years. He rated the pain as 3 after an adjustment but building up to 7 or 8 before the next treatment time. Following supplementation of 12 weeks beginning November, 1995, he rated the pain as a 1 and it only occasionally built prior to adjustment. There was clinically improved intersegmental ROM at the above level and decreased para spinal myospasm which remains stable between treatments for the first time in 10 years.

A 53 year old female presented with cervical spine pain and headache. She had osteoarthritis of the hands with joint enlargement, decreased ROM and mild ulnar deviation. Radiographs revealed cervical spine osteoarthritis. She rated the pain in the cervical spine as 5 and the hands as 7 with inability to knit or do fine work. Following 8 weeks supplementation she had decreased joint enlargement, increased ROM, and rated the pain as a 3 in her hands. Her cervical spine was rated a 3 also. She stated that even her husband has commented on how good her hands look. She had cervical spine manipulation but no hand treatment other than Ginseng of the Sea™.

An 79 year old female presented with severe crippling bilateral hand pain of increasing severity over 1 year. She could only approximate the fingertips to within 3 centimeters of the palm. She had moderate joint edema. She rated the pain as 10. Following supplementation of 8 weeks she began to note improvement. Then in the following 8 weeks she observed significant improvement with improvement of pain and dysfunction. At 18 weeks of supplementation she reported that her pain is 3–4, that she had no swelling in the finger joints, and that all the digits of her right hand touch the palm and all but one of the left fingers could touch the palm.

A 65 year old female presented with chronic knee pain. She rated the pain as a 5 or 6. After six weeks of treatment she reported that the knees are not much improved, but that her chronic arthritis of the proximal interphalangeal joint of the right hand was much better. The edema of the joint was so reduced as to be 50% improved in size with no pain on joint flexion. Following 8 more weeks of supplementation she reported gradual improvement in the knees with pain rating at 3.

A 60 year old male presented with generalized joint discomfort, primarily in the shoulders, neck and upper back. He rated the pain as 4. Following 9 weeks supplementation he rated the pain as 2 and had improved ROM in the involved areas.

A 40 year old male presented with left hip pain. Examination revealed moderate left hip osteoarthritis subsequent to a rollerblading accident 4 years prior. He rated the pain as 5–6 and exacerbating to 8 with increased activity. He also had recurrent left shoulder and neck pain and left knee pain. Following 16 weeks of supplementation beginning in October, 1995 he reported a pain of 1 in his left hip with ability to play basketball without pain. The pain in the left knee was minimal and occasional and there was no left should pain. Remaining cervical spine pain was relieved by cervical manipulation.

A 46 year old male presented with pain the midthoracic spine. He had suffered with this pain since an injury in 1975. Thoracic spine films revealed osteoarthritis of T4, 5, 6 with osteophyte formation in this region. He had been using shark cartilage for 2 years with some relief. He was advised to change to the sea cucumber in place of the shark cartilage and within 2 weeks he noted increased motion without pain. Within 8 weeks he noted that the mid-back did not bother with normal daily activity. He mentioned a significant improvement over the shark cartilage.

As can be seen from the forgoing, all patents treated exhibited significant improvement in subjective evaluation of pain and range of movement after treatment.

EXAMPLE 11

Subjective Benefit from Treatment of Arthritic Inflammation with B1000 and T2000

After testing B1000 in a standard LD50 assay ("FHSA/CPSC Design 16 CFR 1500 Acute Oral Toxicity" (Feb. 3, 1995), Tox Monitor of Oak Park, Ill.) to determine existence of toxicity, finely divided B1000, as obtained by Examples 2 and 3, was mixed with sea cucumber collagen and administered in an average dose of 600 mg per day, corresponding to the inhibition of inflammation at 10 mg/kg that was effective in reducing inflammation in laboratory animals, adjusted for patient weight.

Thirty persons were entered into an open label, non-controlled trial to determine presence or absence of subjective benefit in cases of arthritis inflammation and decreased range of motion.

The trial was conducted by Dr. Michael Aker of Blue Hill, Me., and the results are summarized as follows:

Of the 30 patients enrolled in the trial, 28 patients reported subjective benefit as either increased range of motion or lessened pain and inflammation. Twenty-one of those reporting subjective benefit reported that benefit to be an improvement of more than 75% and seven reported improvements at more than 90%.

I claim:

1. A method for the treatment of inflammatory diseases in a mammal comprising administering an effective dose of a composition comprising an active ingredient selected from the group consisting of isolated sea cucumber body wall, isolated sea cucumber epithelial layer, isolated sea cucumber flower, combinations thereof, active derivatives thereof or combinations of active derivatives thereof.

2. The method of claim 1 wherein the active ingredient is administered in an amount per day between about 10 milligrams per kilogram body weight and 1 gram per kilogram body weight.

3. The method of claim 2 wherein the active ingredient is administered in an amount per day of about 10 milligrams per kilogram body weight.

4. The method of claim 1 wherein the composition is in a dosage form suitable for administration orally, rectally, topically or via injection.

5. The method of claim 4 wherein the dosage form is suitable for oral administration.

6. The method of claim 4 wherein the dosage form is suitable for topical administration.

7. The method of claim 1 wherein the active ingredient is an active deriviative of isolated sea cucumber body wall, isolated sea cucumber epithelial layer or isolated sea cucumber flower selected from the group comprising sulfated polysaccharides, sterol glycosides, saponins, lactones, peptides, protamines, glycogens, saccharides, polysaccharides and combinations thereof.

8. The method of claim 7 wherein the active derivative is a saponin.

9. A method for the treatment of inflammatory diseases in a mammal comprising administering an effective dose of a composition comprising isolated sea cucumber body wall or active derivatives thereof.

10. The method of claim 9 wherein the active ingredient is administered in an amount per day between about 10 milligrams per kilogram body weight and 1 gram per kilogram body weight.

11. The method of claim 10 wherein the active ingredient is administered in an amount per day of about 10 milligrams per kiligram body weight.

12. The method of claim 9 wherein the composition is in a dosage form suitable for administration orally, rectally, topically or via injection.

13. The method of claim 12 wherein the dosage form is suitable for oral administration.

14. The method of claim 12 wherein the dosage form is suitable for topical administration.

15. The method of claim 9 wherein the active ingredient is an active derivative of isolated sea cucumber body wall selected from the group comprising sulfated polysaccharides, sterol glycosides, saponins, lactones, peptides, protamines, glycogens, saccharides, polysaccharides and combinations thereof.

16. The method of claim 15 wherein the active derivative is a saponin.

17. A method for the treatment of inflammatory diseases in a mammal comprising administering an effective dose of a composition comprising isolated sea cucumber epithelial layer or active derivatives thereof.

18. The method of claim 17 wherein the active ingredient is administered in an amount per day between about 10 milligrams per kilogram body weight and 1 gram per kilogram body weight.

19. The method of claim 18 wherein the active ingredient is administered in an amount per day of about 10 milligrams per kilogram body weight.

20. The method of claim 17 wherein the composition is in a dosage form suitable for administration orally, rectally, topically or via injection.

21. The method of claim 20 wherein the dosage form is suitable for oral administration.

22. The method of claim 20 wherein the dosage form is suitable for topical administration.

23. The method of claim 17 wherein the active ingredient is an active derivative of isolated sea cucumber epithelial layer selected from the group comprising sulfated polysaccharides, sterol glycosides, saponins, lactones, peptides, protamines, glycogens, saccharides, polysaccharides and combinations thereof.

24. The method of claim 23 wherein the active derivative is a saponin.

25. A method for the treatment of inflammatory diseases in a mammal comprising administering an effective dose of a composition comprising isolated sea cucumber flower or active derivatives thereof.

26. The method of claim 25 wherein the active ingredient is administered in an amount per day between about 10 milligrams per kilogram body weight and 1 gram per kilogram body weight.

27. The method of claim 26 wherein the active ingredient is administered in an amount per day of about 10 milligrams per kiligram body weight.

28. The method of claim 25 wherein the composition is in a dosage form suitable for administration orally, rectally, topically or via injection.

29. The method of claim 28 wherein the dosage form is suitable for oral administration.

30. The method of claim 28 wherein the dosage form is suitable for topical administration.

31. The method of claim 25 wherein the active ingredient is an active derivative of isolated sea cucumber flower selected from the group comprising sulfated polysaccharides, sterol glycosides, saponins, lactones, peptides, protamines, glycogens, saccharides, polysaccharides and combinations thereof.

32. The method of claim 31 wherein the active derivative is a saponin.

\* \* \* \* \*